(12) United States Patent
Crnkovich et al.

(10) Patent No.: US 8,906,240 B2
(45) Date of Patent: Dec. 9, 2014

(54) EARLY DETECTION OF LOW BICARBONATE LEVEL

(75) Inventors: Martin Joseph Crnkovich, Walnut Creek, CA (US); Aiyuan Wang, San Ramon, CA (US); Fei Wang, Concord, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 389 days.

(21) Appl. No.: 13/220,293

(22) Filed: Aug. 29, 2011

(65) Prior Publication Data

US 2013/0049974 A1   Feb. 28, 2013

(51) Int. Cl.
| | | |
|---|---|---|
| B01D 61/26 | (2006.01) | |
| B01D 61/28 | (2006.01) | |
| B01D 61/30 | (2006.01) | |
| G08B 21/00 | (2006.01) | |
| G06F 19/00 | (2011.01) | |
| A61M 1/16 | (2006.01) | |

(52) U.S. Cl.
CPC ........... *A61M 1/1656* (2013.01); *A61M 1/1668* (2013.01); *A61M 2205/18* (2013.01); *A61M 2205/3327* (2013.01)
USPC ................. 210/746; 210/85; 210/86; 210/97; 210/100; 210/134; 210/252; 210/321.71; 210/739; 340/612; 340/657; 702/19; 702/25

(58) Field of Classification Search
CPC .......... A61M 1/1656; A61M 2205/18; A61M 1/1617; A61M 1/1668; A61M 2205/3327
USPC ............... 210/85, 86, 97, 100, 109, 134, 252, 210/321.6, 321.71, 739, 746; 340/612, 657; 702/19, 25
See application file for complete search history.

(56) References Cited

U.S. PATENT DOCUMENTS

| | | | |
|---|---|---|---|
| 3,871,913 A | | 3/1975 | Shaldon |
| 4,174,231 A | | 11/1979 | Hobgood |
| 4,191,351 A | | 3/1980 | Goyne |
| 4,351,731 A | * | 9/1982 | Perrot ........................... 210/647 |
| 4,469,602 A | * | 9/1984 | Seal .............................. 210/662 |
| 4,581,141 A | | 4/1986 | Ash |

(Continued)

FOREIGN PATENT DOCUMENTS

| | | |
|---|---|---|
| DE | 9418915 U1 | 2/1995 |
| DE | 4422100 C1 | 12/1995 |

(Continued)

OTHER PUBLICATIONS

English translation DE 102008052959 A1 published Apr. 29, 2010.*

(Continued)

*Primary Examiner* — John Kim
(74) *Attorney, Agent, or Firm* — Fish & Richardson P.C.

(57) ABSTRACT

This disclosure relates to early detection of low bicarbonate level. In certain aspects, a method includes receiving a first signal from a conductivity detector connected to a line through which a solution of salt concentrate and fluid flows and determining a first conductivity of the solution based on the first signal. The method also includes receiving a second signal from the conductivity detector at a time after receiving the first signal, determining a second conductivity of the solution based on the second signal, and determining whether the second conductivity is less than the first conductivity by at least a threshold amount.

29 Claims, 5 Drawing Sheets

(56) References Cited

U.S. PATENT DOCUMENTS

| | | |
|---|---|---|
| 4,601,830 A | 7/1986 | Chen |
| 4,666,598 A | 5/1987 | Heath et al. |
| 4,684,460 A | 8/1987 | Issautier |
| 4,728,496 A | 3/1988 | Petersen et al. |
| 4,770,787 A | 9/1988 | Heath et al. |
| 4,784,495 A | 11/1988 | Jonsson et al. |
| 4,789,467 A | 12/1988 | Lindsay et al. |
| 4,997,577 A | 3/1991 | Stewart |
| 5,256,371 A | 10/1993 | Pippert |
| 5,262,068 A | 11/1993 | Bowers et al. |
| 5,277,820 A | 1/1994 | Ash |
| 5,304,349 A | 4/1994 | Polaschegg |
| 5,409,612 A | 4/1995 | Maltais et al. |
| 5,421,813 A | 6/1995 | Ohnishi |
| 5,487,827 A * | 1/1996 | Peterson et al. .............. 210/87 |
| 5,536,412 A | 7/1996 | Ash |
| 5,589,070 A | 12/1996 | Maltais et al. |
| 5,591,344 A | 1/1997 | Kenley et al. |
| 5,603,902 A | 2/1997 | Maltais et al. |
| 5,605,630 A | 2/1997 | Shibata |
| 5,629,871 A * | 5/1997 | Love et al. .............. 702/34 |
| 5,713,125 A | 2/1998 | Watanabe et al. |
| 5,788,099 A | 8/1998 | Treu et al. |
| 5,919,369 A | 7/1999 | Ash |
| 5,944,684 A | 8/1999 | Roberts et al. |
| 5,972,223 A * | 10/1999 | Jonsson et al. .............. 210/647 |
| 6,000,567 A | 12/1999 | Carlsson et al. |
| 6,036,858 A | 3/2000 | Carlsson et al. |
| 6,086,753 A | 7/2000 | Ericson et al. |
| 6,143,181 A | 11/2000 | Falkvall et al. |
| 6,170,785 B1 | 1/2001 | Lampropoulos |
| 6,190,855 B1 | 2/2001 | Herman et al. |
| 6,277,277 B1 | 8/2001 | Jacobi et al. |
| 6,280,632 B1 | 8/2001 | Polaschegg |
| 6,308,721 B1 | 10/2001 | Bock et al. |
| 6,409,699 B1 | 6/2002 | Ash |
| 6,416,293 B1 | 7/2002 | Bouchard et al. |
| 6,428,706 B1 | 8/2002 | Rosenqvist et al. |
| 6,755,976 B2 | 6/2004 | Rosenqvist et al. |
| 6,878,283 B2 | 4/2005 | Thompson |
| 7,033,498 B2 | 4/2006 | Wong |
| 7,077,956 B2 | 7/2006 | Rovatti |
| 7,241,272 B2 | 7/2007 | Karoor et al. |
| 7,947,179 B2 | 5/2011 | Rosenbaum et al. |
| 2002/0079695 A1 | 6/2002 | Campbell et al. |
| 2003/0105424 A1 | 6/2003 | Karoor et al. |
| 2004/0019312 A1 | 1/2004 | Childers et al. |
| 2004/0050789 A1 | 3/2004 | Ash |
| 2005/0274658 A1 | 12/2005 | Rosenbaum et al. |
| 2007/0158247 A1 | 7/2007 | Carr et al. |
| 2007/0158249 A1 | 7/2007 | Ash |
| 2007/0158268 A1 | 7/2007 | DeComo |
| 2007/0161113 A1 | 7/2007 | Ash |
| 2007/0161941 A1 | 7/2007 | Ash et al. |
| 2007/0181499 A1 | 8/2007 | Roberts et al. |
| 2008/0149563 A1 | 6/2008 | Ash |
| 2008/0177216 A1 | 7/2008 | Ash |
| 2008/0230450 A1 * | 9/2008 | Burbank et al. .............. 210/92 |
| 2009/0114595 A1 | 5/2009 | Wallenas et al. |

FOREIGN PATENT DOCUMENTS

| | | |
|---|---|---|
| EP | 0 278 100 | 8/1988 |
| EP | 0714668 A1 | 6/1995 |
| EP | 0 673 658 | 9/1995 |
| EP | 1 342 480 | 9/2003 |
| EP | 1 096 991 | 6/2004 |
| WO | WO 97/02055 | 1/1997 |
| WO | WO 97/02056 | 1/1997 |
| WO | WO 98/17333 | 4/1998 |
| WO | WO 99/37342 | 7/1999 |
| WO | WO 02/30267 | 4/2002 |
| WO | WO 02/43859 | 6/2002 |
| WO | WO 2005/123230 | 12/2005 |
| WO | WO 2007/028056 | 3/2007 |
| WO | WO 2007/081383 | 7/2007 |
| WO | WO 2007/081384 | 7/2007 |
| WO | WO 2007/081565 | 7/2007 |
| WO | WO 2007/081576 | 7/2007 |
| WO | WO2010045934 A3 | 6/2010 |

OTHER PUBLICATIONS

Notification of Transmittal of the International Search Report and the Written Opinion of the International Searching Authority for corresponding PCT Application No. PCT/US2012/050085, mailed Dec. 19, 2012, 11 pages.

"*RX Guide to Custom Dialysis*," COBE Renal Care Inc., Revision E. Sep. 1993.

"*Sorbent Dialysis Pimer*," COBE Renal Care, Inc., Sep. 4, 1993 Ed. Blumenkrantz et al., "*Artif Organs*," 3(3):230-236, 1978.

Operator's Manual—Fresenius 2008K Hemodialysis Machine (2000).

\* cited by examiner

EARLY DETECTION OF LOW BICARBONATE LEVEL

TECHNICAL FIELD

This invention relates to early detection of low bicarbonate level.

BACKGROUND

Renal dysfunction or failure and, in particular, end-stage renal disease, causes the body to lose the ability to remove water and minerals and excrete harmful metabolites, maintain acid-base balance and control electrolyte and mineral concentrations within physiological ranges. Toxic uremic waste metabolites, including urea, creatinine, and uric acid, accumulate in the body's tissues which can result in a person's death if the filtration function of the kidney is not replaced.

Dialysis is commonly used to replace kidney function by removing these waste toxins and excess water. In one type of dialysis treatment—hemodialysis—toxins are filtered from a patient's blood externally in a hemodialysis machine. Blood passes from the patient through a dialyzer separated by a semi-permeable membrane from a large volume of externally-supplied dialysis solution. The waste and toxins dialyze out of the blood through the semi-permeable membrane into the dialysis solution, which is then discarded.

The dialysis solutions or dialysates used during hemodialysis typically contain sodium chloride and other electrolytes, such as calcium chloride, or potassium chloride, a buffer substance, such as bicarbonate, or acetate and acid to establish a physiological pH, plus optionally, glucose or another osmotic agent.

SUMMARY

In one aspect of the invention, a method includes receiving a first signal from a conductivity detector connected to a line through which a solution of salt concentrate and fluid flows and determining a first conductivity of the solution based on the first signal. The method also includes receiving a second signal from the conductivity detector at a time after receiving the first signal, determining a second conductivity of the solution based on the second signal, and determining whether the second conductivity is less than the first conductivity by at least a threshold amount.

In another aspect of the invention, a dialysis system includes a container containing a salt concentrate, a line connected to the container, a conductivity detector connected to the line, and a data processing apparatus connected to the conductivity detector. The data processing apparatus are configured for receiving a first signal from a conductivity detector connected to a line through which a solution of salt concentrate and fluid flows and determining a first conductivity of the solution based on the first signal. The data processing apparatus are configured also for receiving a second signal from the conductivity detector at a time after receiving the first signal, determining a second conductivity of the solution based on the second signal, and determining whether the second conductivity is less than the first conductivity by at least a threshold amount.

Implementations can include one or more of the following features.

In certain implementations, the method also includes based on a determination that the second conductivity is less than the first conductivity by at least the threshold amount, providing an alert to a user.

In some implementations, the alert is provided to the user at a period of time before a container containing the salt concentrate is empty.

In some implementations, the alert prompts the user to replace the container.

In certain implementations, the method also includes based on a determination that the second conductivity is less than the first conductivity by at least the threshold amount, receiving a third signal from the conductivity detector at a time after receiving the second signal and determining a third conductivity of the solution based on the third signal. The method also includes determining whether the third conductivity is less than the second conductivity by at least a threshold amount, and based on a determination that the third conductivity is less than the second conductivity by at least the threshold amount, providing an alert to a user.

In some implementations, determining each conductivity of the solution based on each respective signal includes adjusting a conductivity measurement of the solution based on the signal from the conductivity detector and a temperature of the solution.

In some implementations, the method also includes receiving a signal from a temperature detector connected to the line and determining the temperature of the solution based on the signal received from the temperature detector.

In some implementations, the method also includes storing the first conductivity for comparison to the second conductivity.

In certain implementations, storing the first conductivity includes receiving a preceding signal from the conductivity detector at a time prior to receiving the first signal, determining a preceding conductivity of the solution based on the signal, and determining that a difference between the first conductivity and the preceding conductivity is within a threshold amount. The method also includes based on the determination that the difference between the first conductivity and the preceding conductivity is within the threshold amount, storing the first conductivity for comparing to the second conductivity.

In some implementations, storing the first conductivity further includes comparing the first conductivity to a threshold conductivity, and based on a determination that the first conductivity meets the threshold conductivity, storing the first conductivity.

In some implementations, the container is a collapsible bag.

Implementations can include one or more of the following advantages.

In some implementations, the methods described provide early detection of a low level of bicarbonate in a dialysis system. As the dialysis process may take a relatively long amount of time, receiving an early indication that the bicarbonate level is running low can allow an operator of the system not to have to continually monitor the bicarbonate level throughout the length of the process. As such, the operator can focus more of his or her attention on other concerns related to the dialysis process. The operator can also prepare the machine for another bag or the end of the process with an early indication, reducing (e.g., minimizing) downtime of the machine.

DETAILED DESCRIPTION

In general, the invention relates to systems and methods for early detection of low bicarbonate level in a dialysis system. In some aspects of the invention, a hemodialysis system includes a controller that controls the hemodialysis system, to carry out a hemodialysis treatment. The controller receives signals from a conductivity detector connected to a fluid line through which a bicarbonate solution passes. By monitoring the conductivity of the solution, early detection of a low level of bicarbonate can be provided to the user.

Figure 1:
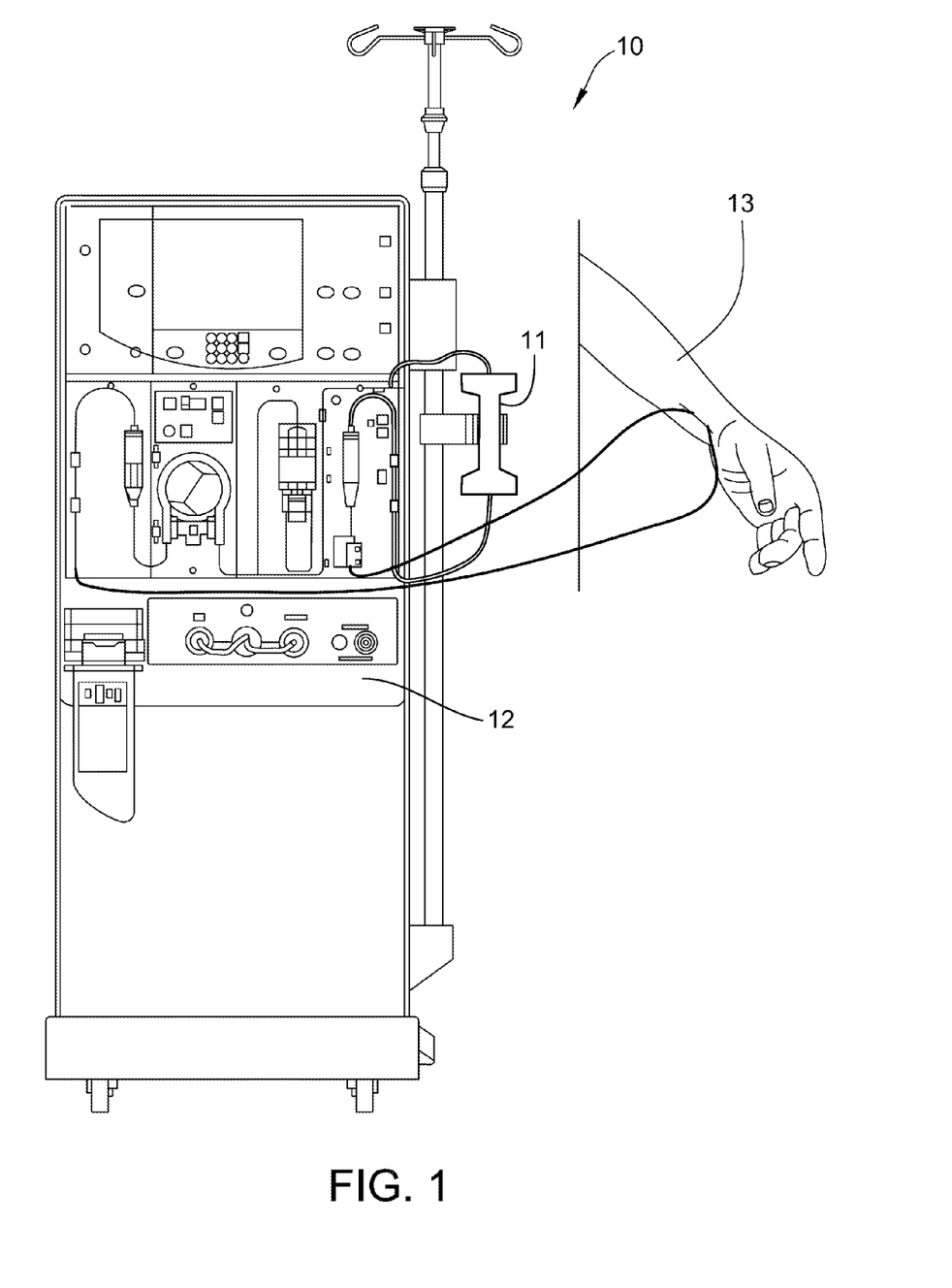
FIG. 1 is a schematic diagram of a hemodialysis system that is connected to a patient.

Referring to FIG. 1, a dialysis system 10 includes a dialysis machine 12 that includes a subsystem 15 for preparing a salt solution from a powdered salt concentrate to form dialysate. During treatment a disposable fluid line set and a dialyzer 11 is connected to the machine 12 and to a patient 13 to permit the patient's blood to circulate through the fluid line set and dialyzer 11. Fluid lines also extend from the machine 12 to the dialyzer 11 to allow the dialysate to pass through the dialyzer 11 with the blood. As the blood and dialysate pass through the dialyzer 11, toxins move across a semi-permeable surface of the dialyzer 11 from the blood to the dialysate.

Figure 2:
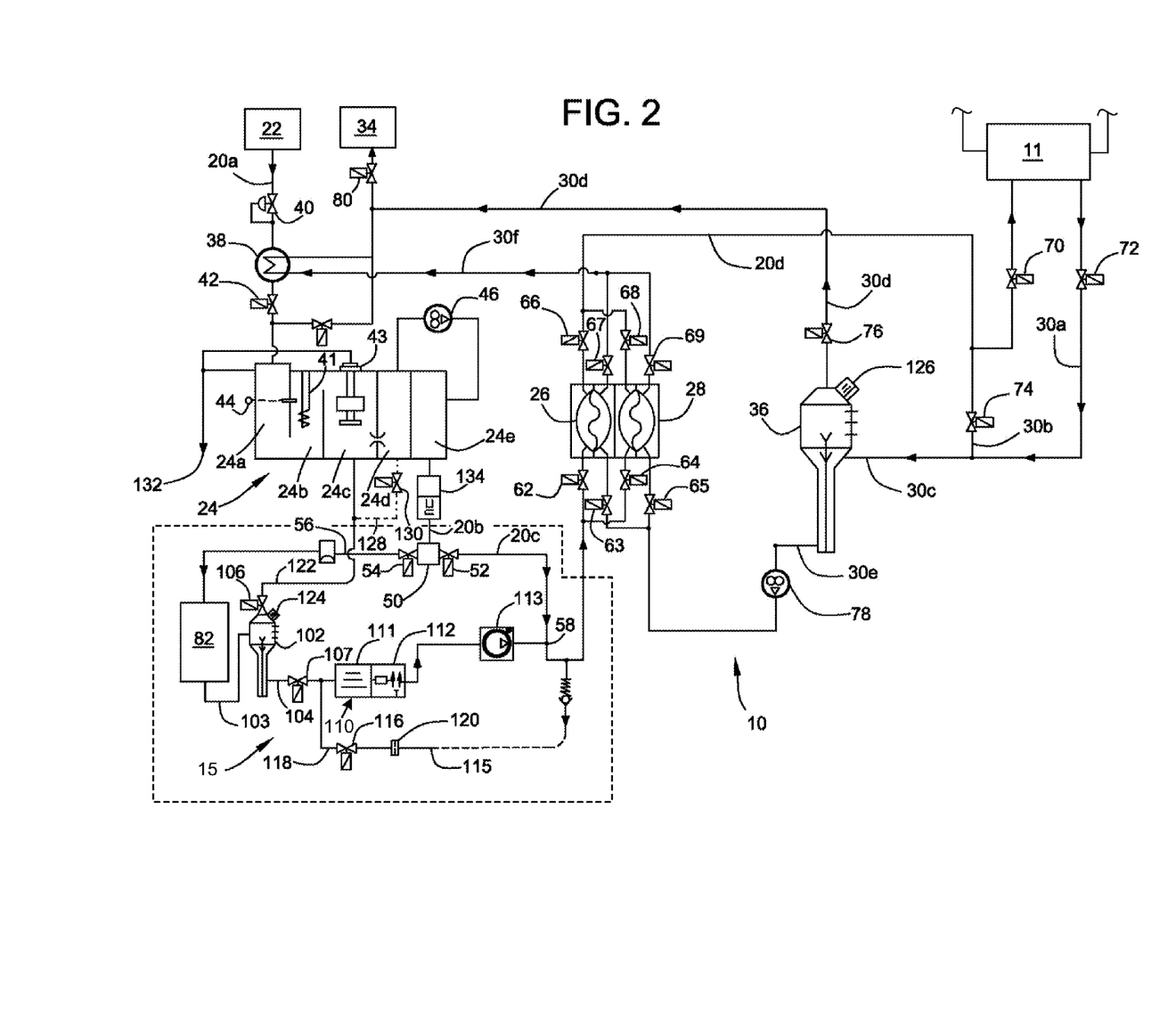
FIG. 2 is a schematic diagram of a dialysate circuit and associated components of the hemodialysis system of FIG. 1.

FIG. 2 illustrates a representative hydraulic arrangement of the dialysis system 10. Many of the illustrated components are housed inside the machine 12 and are thus not visible in FIG. 1. By way of a general overview of the operation, the system 10 includes main fluid line segments 20a-d (collectively referred to as a mainline 20) that are fluidly coupled to a fluid source 22 at one end, and to the dialyzer 11 at the other end, with various optional assemblies disposed along the mainline 20. In some implementations, optional assemblies are disposed along the mainline 20 for preparing the salt solution or dialysate and may include a hydroblock 24 and one or more balancing chambers 26, 28.

Line segments 30a-f (collectively referred to as a return line 30) from the dialyzer 11 provides return flow from the dialyzer 11 to a drain 34. Subassemblies such as an air separation chamber 36 and a heat exchanger 38 are provided along the return line 30. It is noted that not all elements of the illustrated hydraulic arrangement are necessary to the structure and operation of the subsystem 15 for preparing a salt solution from a powdered salt concentrate, although a general explanation is provided herein in the interest of completeness.

Turning now to the specifics of the illustrated hydraulic arrangement, the fluid source 22 includes any appropriate type of fluid or fluids, such as a reverse osmosis fluid (RO fluid) source. Fluid from the fluid source 22 flows through mainline segment 20a to the hydroblock 24. In some implementations, the heat exchanger 38, a pressure regulator 40, and a control valve 42 are provided along the mainline segment 20a between the fluid source 22 and the hydroblock 24. The heat exchanger 38 heats the fluid somewhat with heat from the return spent fluid, as will be discussed below.

The hydroblock 24 is a multichambered unit (chambers 24a-24e being illustrated). The fluid is heated by a heater 41 in chamber 24b and vented to a vent 43 in chamber 24c as the fluid flows through the various chambers 24a-e of the hydroblock 24. The fluid temperature within the hydroblock 24 is monitored and/or controlled by a control thermostat 44. A deaeration pump 46 pumps fluid between the forth and fifth chambers 24d, 24e of the hydroblock 24 to return the fluid to the mainline segment 20b.

Leaving the hydroblock 24, the mainline segment 20b bifurcates at a branch point 50. Valves 52, 54 control the flow of fluid to the continuing mainline segment 20c and a subsystem line 56, respectively. If the valve 54 is closed and valve 52 open, the fluid continues through the valve 52 to the mainline segment 20c. Conversely, if the valve 54 is open and the valve 52 closed, fluid proceeds through valve 54 to the subsystem line 56. As with all of the valves in this disclosure, the valves 52, 54 may be simple shut-off valves, or other multiposition valves. For example, valves 52, 54 may be replaced by a single valve that includes positions that arrest flow entirely, that direct flow to the subsystem line 56, or that direct flow along the mainline segment 20c.

The subsystem line 56 connects flow from the mainline segment 20b to the subsystem 15 for preparing a salt solution, as will be explained in greater detail below. After leaving the subsystem 15, the salt solution is returned to the mainline segment 20c at junction 58. The continuing mainline segment 20c directs flow to the balance chambers 26, 28. Flow through the balancing chambers 26, 28 is controlled by valves 62-69. Each of the balancing chambers 26, 28 includes two separate subchambers separated by a flexible membrane, the significance of which will be discussed below. Flow from the subsystem 15 flows into the respective balancing chambers 26, 28 through valves 62 and 64, and out from the balancing chambers 26, 28 through valves 66, 68. Valves 63, 65, 67, and 69 control flow of spent fluid, as further described below.

Leaving the balancing chambers 26, 28, the solution is directed through mainline segment 20d. Flow to and from the dialyzer 11 is controlled by a pair of control valves 70, 72 disposed along the mainline segment 20d and the return line segment 30a, respectively, as well as a bypass valve 74 disposed in bypass line 30b between the mainline segment 20d and the return line segment 30a. Thus, fluid from the balancing chambers 26, 28 flowing through mainline segment 20d moves on to the dialyzer 11 when dialyzer inlet valve 70 is in the open configuration and bypass valve 74 in the bypass line 30b is in the closed position.

As the dialysate solution flows through the dialyzer 11 so does a patient's blood. As a result, toxins, such as urea, are transferred across a semi-permeable structure (e.g., semi-permeable microtubes) of the dialyzer 11 from the patient's blood to the dialysate.

Following the dialyzer 11, spent fluid passes the control valve 72 to return to the machine 12 through return line segments 30a and 30c with the bypass valve 74 in the closed position. To ensure accurate operation of the balancing chambers 26, 28, as discussed below, spent fluid passes into the air separation chamber 36 before reaching the balance chambers 26 and 28. From the air separation chamber 36, separated gases, and potentially fluid, are passed through return line segment 30d to the drain 34 by opening shutoff valves 76 and 80. Return fluid, from which the gases have been separated in the air separation chamber 36, may be pumped by flow pump 78 through return line segment 30e to one or both of the balance chambers 26, 28 through valves 63, 65. Leaving the balance chambers 26, 28 through valves 67, 69, respectively, the spent fluid is directed to a heat exchanger 38 and the drain 34 by way of return line segment 30f. Overall flow to the drain 34 is controlled by shutoff valve 80.

Within the balance chambers 26, 28, fresh fluid from the subsystem 15 passes along one side of the internal membranes, while spent fluid passes along the other side of the internal membranes. Pumping of spent fluid from line segment 30e along one side of the membrane with fresh fluid passing along the other side of the membrane from mainline segment 20c results in a balanced provision of fluid from and to the dialyzer 11 during use.

The structure and operation of the subsystem 15 for preparation of a salt solution will now be explained. Still referring to FIG. 2, fluid flowing through the mainline segment 20b from the hydroblock 24 is directed to the subsystem 15 by opening the control valve 54 and closing the control valve 52 at adjacent junction 50 to provide flow to the subsystem line 56. To prepare the salt solution, fluid from the subsystem line 56 enters a bag 82, which contains a powdered salt concentrate. The bag 82 can, for example, be a collapsible, replaceable bag that encloses the powdered salt concentrate.

Figure 3:
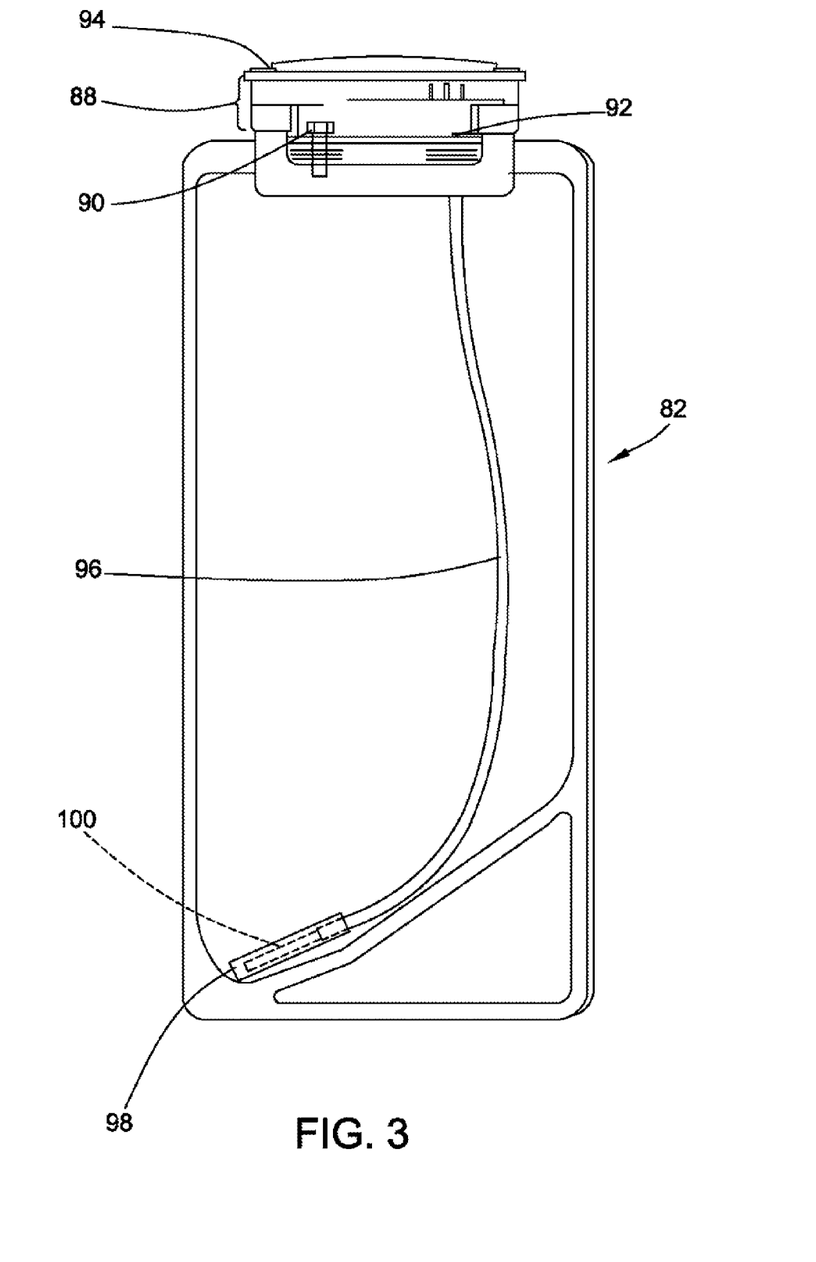
FIG. 3 is a representative partially cross-sectioned view of a collapsible bag of the hemodialysis system of FIG. 1 that contains a powdered salt concentrate.

An example of a suitable bag 82 is shown in FIG. 3. In this partially cross-sectioned view, the bag 82 includes a protective cover 94. In some implementations, the bag 82 is coupled to the subsystem 15 by a connector 88 having an inlet 90 and an outlet 92. Although the inlet 90 and outlet 92 are shown in an upper portion of the bag 82, the inlet 90 and outlet 92 may be disposed elsewhere, so long as the requisite mixing is obtained. For example, the inlet may be disposed in a lower portion of the bag 82 to allow the fluid to be injected upward into the bag 82 to encourage agitation to facilitate mixing.

In order to allow the mixed salt solution to be withdrawn from the bag 82 when it is not completely full, the outlet 92 originates below the level of fluid in the bag 82. In some implementations, a tube 96 having a lower opening 98 is fluidly coupled to the outlet 92 such that the opening 98 is disposed in a lower portion of the bag 82, that is, below the fluid level. To inhibit the intake of powdered salt that is not yet dissolved, a filter 100 is disposed at the opening 98. The filter 100 is made of any appropriate material, such as, for example, porous polyethylene. The bag 82 and connector 88 are made of high density polyethylene.

The bag 82 contains a dry form of one or more of any suitable salts used for preparation of dialysis solution. By way of example only, such suitable salts include sodium bicarbonate and sodium acetate. Carbon dioxide will typically be generated from the initial contact between the fluid and the bicarbonate powder. Residual air is likewise often disposed within the bag 82. As explained above, in order to provide proper removal of the salt solution from the bag 82, the opening 98 into the outlet 92 of the bag 82 is maintained below the surface of the fluid contained therein. It will thus be appreciated that a reduction of gases disposed within the bag 82 typically provides more space for the introduction of fluid.

Returning to FIG. 2, in order to expel air from the subsystem 15, an air separation chamber 102 is provided downstream of the bag 82. The air separation chamber 102, which is fluidly connected to the bag 82 by a subsystem line 103, is designed to remove both air residually disposed within the bag 82 and gases precipitating out of the bicarbonate solution during operation of the subsystem 15. During operation, air rises to the top of the air separation chamber 102, while the bicarbonate solution settles to the bottom of the air separation chamber 102. In use, bicarbonate solution is passed from the air separation chamber 102 to subsystem line 104, while gases are passed from the air separation chamber 102 by operation of valve 106.

Turning first to the passage of bicarbonate solution from the air separation chamber 102, flow through the subsystem line 104 is controlled by operation of a valve 107. When valve 107 is in the open position and valve 106 is in the closed position, bicarbonate solution flows through subsystem line 104 to a conductivity detector 110 that includes a conductivity cell 111 and a temperature detector 112. In some implementations, the temperature detector 112 is a thermistor, which is a resistor in which the resistance varies significantly with temperature. The conductivity cell 111 measures the conductivity of or provides a representative reading of the bicarbonate level of solution leaving the air separation chamber 102. From the conductivity cell 111 and temperature detector 112, a bicarbonate pump 113 pumps the bicarbonate solution to rejoin the mainline segment 20c at junction 58, via which the bicarbonate solution is passed to one or both of the balancing chambers 26, 28, and on to the dialyzer 11. The conductivity detector 110 is used to provide early detection of a low bicarbonate level in the bag 82, and thus allows the operator to efficiently address such an issue, as described in greater detail below.

During normal operation, the air separation chamber 102 separates gas from fluid in the bicarbonate solution progressing to the junction 58 for delivery to the dialyzer 11, while the air separation chamber 36 separates gas from spent fluid returning from the dialyzer 11. It will be appreciated that this elimination of the gases in the fluids flowing to and from the dialyzer 11 facilitates efficient and accurate operation of the balancing chambers 26, 28 during regular operation of the system 10.

In order to determine if and when gas has accumulated in the air separation chamber 102, an air sensor 124 is provided in the air separation chamber 102. In some implementations, the air sensor 124 is a two-pronged air detection probe located at the top of the air separation chamber 102 such that an electric current between the two prongs is detected when fluid fills the chamber 102 to at least the level of the prongs. Conversely, when there is air in the chamber 102, the air between the two prongs acts as an insulator and electric current does not flow. A similar air sensor 126 is provided in air separation chamber 36 to provide an indication of when valve 76 should be opened to allow passage of gases from air separation chamber 36 to return line segment 30d.

Flow through the air separation chamber 102 is controlled by the control valve 106. If air is not detected in the air separation chamber 102, the control valve 106 is closed, and the solution proceeds through subsystem line 104, advanced by the pump 113 to rejoin the mainline segment 20c at junction 58. The solution is then passed on to the balance chambers 26, 28 and to the mainline segment 20d for delivery to the dialyzer 11, as explained above.

Conversely, if the air sensor 124 detects air in the air separation chamber 102, the control valve 106 is opened to vent gases from the air separation chamber 102 to degassing line 122. The degassing line 122 provides a fluid connection to the hydrochamber 24 such that gases accumulated in the air separation chamber 102 are passed to the hydrochamber 24. The degassing line 122 is connected to the third chamber 24c of the hydrochamber 24. In use, only gases typically are released from the separation chamber 102 through the valve 106 for very short periods of time, rather than an air/sodium bicarbonate solution combination.

Some implementations further include a bypass line 128 in which a valve 130 is disposed, coupling the degassing line 122 to the fourth chamber 24d. During cleaning modes of the machine, the valve 130 is opened in order to relieve pressure built up within the hydrochamber 24.

To assist in the separation of gases from the fluid contained within the hydrochamber 24, the third chamber 24c of the hydrochamber 24 includes a venting structure 43. Gases entering the third chamber 24c from the degassing line 122 rise upward through the fluid contained within the hydrochamber 24 to the upper portion of the third chamber 24c to be vented through the venting structure 43 to a drain or the atmosphere 132.

Under normal operation, only gases are typically vented from the air separation chamber 102 through the degassing line 122 to the hydrochamber 24. In order to ensure that the valve 106 and air sensor 124 are operating properly, that is, in order to monitor whether any of the sodium bicarbonate solution is being vented from the air separation chamber 102 to the hydrochamber 24 through the degassing line 122, a conductivity sensor 134 is provided between the hydrochamber 24 and the bag 82. In this way, a direct conductivity number is determined for the fluid as it flows from the hydrochamber 24 to the mainline segment 20c or subsystem line 56.

According to the disclosed method, the measured conductivity number is compared to a reference conductivity number for fluid that is not diluted with a sodium bicarbonate solution. If the measured conductivity number differs from the reference conductivity by greater than a given amount or percentage, or if the measured conductivity number does not fall within a predetermined reference range, then further corrective action is taken. Further corrective action may include, by way of example, shutting down the system 10 or providing a warning light or the like that the subsystem 15, the air separation chamber 102, the valve 106, and/or the sensor 124 must be checked.

The conductivity sensor 134 is also utilized to supply a measured conductivity number to a controller with regard to the fluid conductivity, as opposed to an estimated conductivity number, which is often utilized in calculations related to operation of dialysis systems. For example, such systems often assume that the fluid, e.g., water, has no conductivity. The measured conductivity number provided by the conductivity sensor 134 for fluid leaving the hydrochamber 24 is utilized in system calculations as opposed to an assumed or estimated conductivity number. As a result, a more accurate conductivity number can be used.

The system 10 may include one or more controllers (not illustrated), which are capable of receiving signals from and activating one or more of the pumps 46, 78, 113 and one or more of the valves 42, 52, 54, 62-70, 72, 74, 76, 80, 106, 107, 116, 130, and receiving input from air sensors 124, 126, and conductivity detector 110, conductivity cell 111, temperature detector 112, and conductivity sensor 134. For example, in some implementations, a Microchip PIC18F6410 (manufactured by Microchip Technology, Inc. (Chandler, Ariz.)) is used for the controller.

During treatment, fluid, typically purified water, is delivered from the hydrochamber 24 to the bag 82. The water mixes with the solid bicarbonate in the bag 82 to produce the bicarbonate solution used as the dialysate. The dialysate is delivered to the dialyzer 11 via the balancing chambers 26, 28, which ensure that the volume of dialysate delivered to the dialyzer 11 is approximately equal to the volume of spent dialysate exiting the dialyzer 11. The dialysate passes through the dialyzer 11 along with a patient's blood to filter the blood and remove toxins from the blood. The spent dialysate containing the removed toxins is then sent to the drain 34 via the balancing chambers 26, 28.

Figure 4:
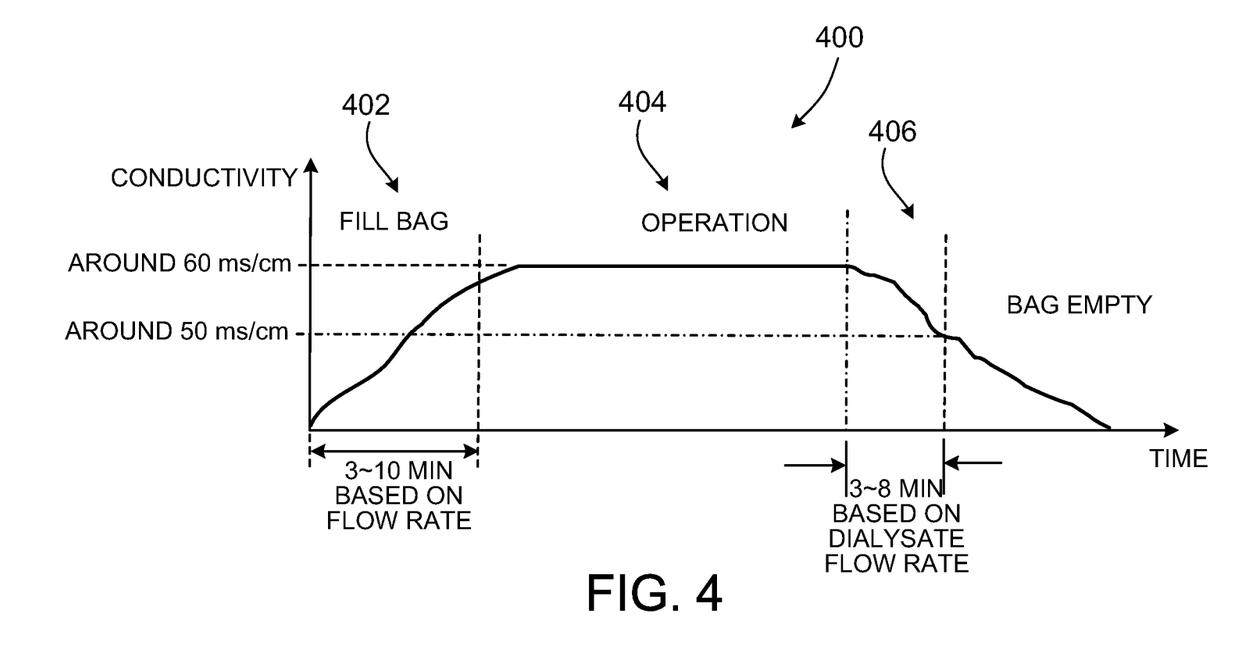
FIG. 4 is a graph depicting the conductivity of a solution flowing from the collapsible bag of the hemodialysis system of FIG. 1 during a dialysis treatment.

Referring to FIG. 4, an example conductivity level of the bicarbonate solution during operation of the machine is shown. At the beginning portion 402 of the operation, the bag 82 is being filled with purified water to produce the dialysate. During this beginning portion 402, the conductivity of the bicarbonate solution rises, for example, from 0 mS/cm to about 60 mS/cm. The beginning portion 402 lasts, for example, about three to ten minutes, depending on the flow rate of the purified water into the bag 82.

During the middle portion 404 of the operation of the machine, the dialysate is passed through the dialyzer 11 along with blood of the patient to perform the dialysis treatment. The conductivity of the bicarbonate solution remains at a relatively high and steady level (e.g., around 60 mS/cm) during this middle portion 404. The relatively high and steady level lasts for the majority of the operation of the machine.

As the solid bicarbonate is depleted, the solution becomes more diluted towards the end portion 406 of the operation. Accordingly, the conductivity of the solution decreases, for example, to 0 mS/cm, as the solution increases in ratio of fluid to bicarbonate. Thus, by monitoring the conductivity of the solution with conductivity detector 110, an early indication can be provided that the bicarbonate level is lowering to a point where the bag 82 will have to be replaced or the operation will be complete.

Figure 5:
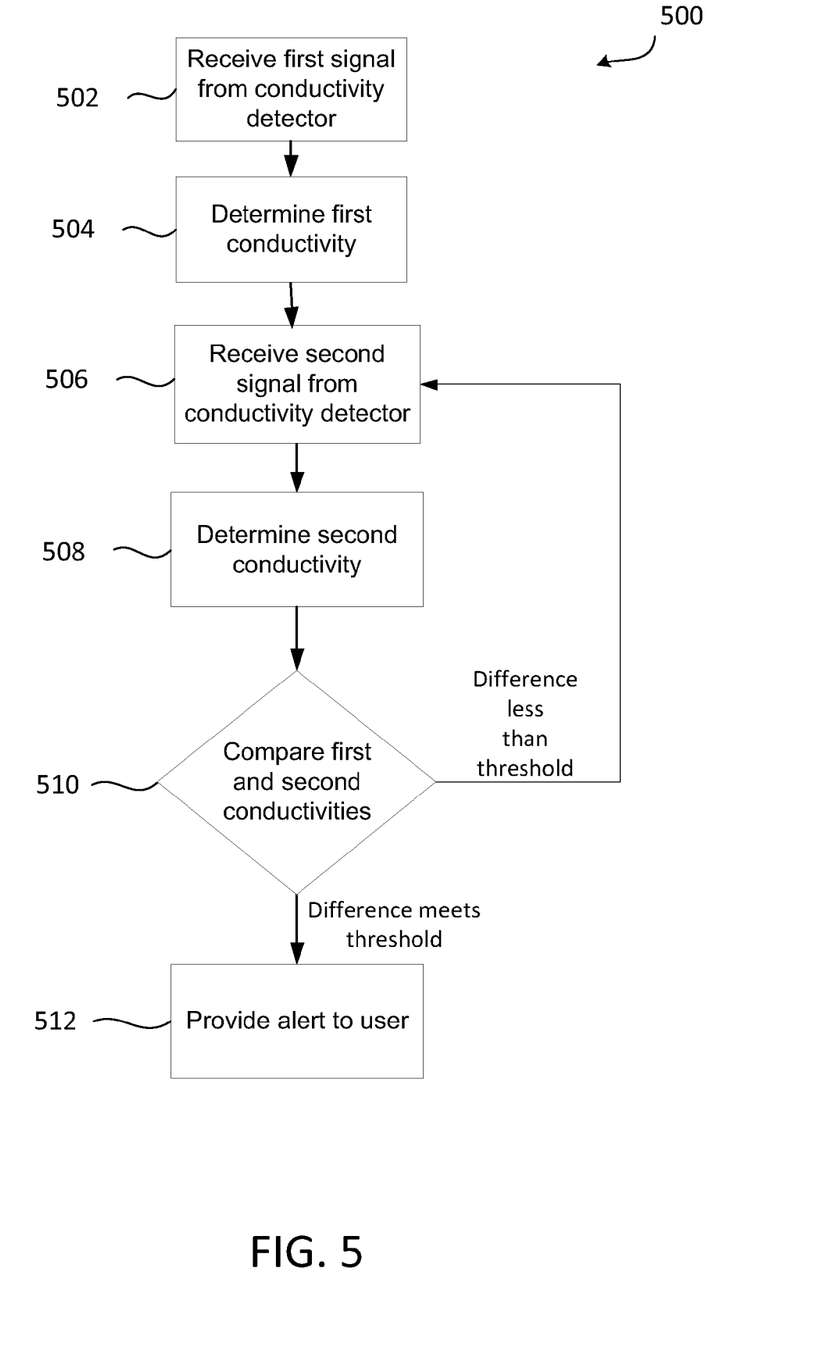
FIG. 5 is a flow chart depicting a method of early detection of a low bicarbonate level in a solution flowing from the collapsible bag of the hemodialysis system of FIG. 1.

FIG. 5 is a flow chart illustrating a method of early detection of a low bicarbonate level. Referring to FIG. 5, the controller receives a first signal from the conductivity detector 110 (502). The first signal is received a period of time after the start of the dialysis process. For example, the first signal can be received about ten to fifteen minutes after the beginning of the operation. The controller determines a first conductivity of the bicarbonate solution from the first signal (504). The first conductivity can be used as a baseline measure against which later measurements can be compared. Using the first conductivity to compare later levels, rather than a fixed, or even adjustable magnitude can allow for discrepancies between conductivity detectors 110 and dialysis systems 10. For example, some conductivity detectors on some dialysis systems might be more sensitive than other conductivity sensors, or calibrated differently to produce a reading that is not typical (e.g., not around 60 mS/cm for the middle portion of the operation of the machine). By using the reading provided by the conductivity sensor as the baseline, a relative drop in conductivity is still detected as the bag 82 runs out of bicarbonate to provide an early alert to the operator of the machine.

At a time after receiving the first signal, a second signal is received from the conductivity detector (506). The controller determines a second conductivity of the bicarbonate solution from the second signal (508). The controller compares the first and second conductivities (510). If the second conductivity is less than the first conductivity by more than a threshold amount (e.g., about 10 ms/cm), it is determined that the bicarbonate is running low in the bag 82 and an alert is provided to an operator of the system (512). The alert can include a sound, an alarm, a message on a display of the dialysis system 10 or other appropriate visual/audio indication. For example, the controller can send signals to speakers and/or a visual display to provide an appropriate audio/visual indication.

If the second conductivity is not less than the first conductivity by more than a threshold amount, another second conductivity is determined at a later time. For example, the controller can wait one minute before receiving another second signal from the conductivity detector 110 to determine another second conductivity to compare to the first conductivity.

The conductivity cell 111 used in the conductivity detector 110 is configured to measure conductivity of solutions at a specific temperature (e.g., 25 degrees Celsius). The temperature of the bicarbonate solution, however, varies as it is being raised to be passed through the dialyzer 11 to the patient. Therefore, the conductivity of the dialysate is determined by adjusting the signal received from the conductivity detector 110 and the temperature of the solution. The amount of adjustment can be determined using equations that approximate temperature dependence of conductivity (e.g., the Steinhart-Hart equation).

While an implementation of a method for early detection of low bicarbonate level has been described above, alternative or additional steps can be included. For example, in some implementations, before providing an alert to the operator, a third conductivity signal is received from the conductivity detector 110, after the second conductivity is determined to be at least a threshold level less than the first conductivity. The third conductivity is compared to the second conductivity to ensure the conductivity of the solution is, in fact, decreasing towards zero, rather than the second conductivity being an anomalous measurement or dip in conductivity. If the third conductivity is not less than the second conductivity by a threshold amount, another conductivity can be measured at a later time. Alternatively or additionally, another conductivity can be measured to determine whether the conductivity of the solution is still at a decreased level from the first conductivity.

In some implementations, the controller stores the first conductivity measurement so that it can compare the second conductivity to the first conductivity to determine whether the bicarbonate is running low. Before storing the first conductivity measurement, the controller receives signals from the conductivity sensor and determines conductivities of the solution to ensure the conductivity is not still increasing (e.g., during the initial stage when the bicarbonate bag is being filled with fluid). Once the conductivity of the solution reaches a relatively steady state, the controller can store the conductivity measurement as a first conductivity measurement. For example, if a conductivity measurement is taken that is higher than the stored first conductivity measurement, the new, higher conductivity measurement can replace the stored first conductivity measurement.

In some implementations, a minimum predetermined conductivity threshold can be used for the first conductivity, such that if the first conductivity is below the minimum predetermined conductivity threshold (e.g., about 40-50 ms/cm), another first conductivity can be measured at a later time.

In some implementations, the temperature adjustment of the conductivity measure can be determined by a stored lookup table that provides conductivities relative to temperatures.

While the fluid referenced in this disclosure as being introduced to the bag 82 to form the bicarbonate solution or dialysate will typically be purified water, it is intended that the terms "fluid" and "fluids" will encompass other appropriate fluids for the purposes of the disclosed method and arrangement.

As used in this disclosure, the term "air separation chamber" is used to signify a structure that allows the separation of gases from a solution, and permits the separate removal of each through respective outlets. Further, as used in this disclosure, the term "gas" or "gases" is not limited to air, but may include other gases, such as carbon dioxide, etc.

While the valve 42 illustrated in FIG. 2 has been described as being used to overall flow to the mainline segment 20a, the pressure regulator 40 may alternately or additionally control the pressure of the fluid (and thus the flow of the fluid) as it passes through the section of the mainline segment 20a.

While the bag 82 has been described as a flexible bag, any other appropriate structure may alternatively be used. For example, a rigid container, a semiflexible container, or a flexible container can be used.

While the venting structure 43 is described to be included in the third chamber 24c of the hydrochamber 24, other venting structures can be included in other chambers.

While only one controller is described, multiple controllers may alternatively be used.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, for example, a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (for example, multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, for example, an FPGA (field programmable gate array) or an ASIC (application specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (for example, one or more scripts stored in a markup language document), in a single file dedicated to the program in question, or in multiple coordinated files (for example, files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, for example, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, for example, magnetic, magneto optical disks, or optical disks. However, a computer need not have such devices. Moreover, a computer can be embedded in another device, for example, a mobile telephone, a personal digital assistant (PDA), a mobile audio or video player, a game console, a Global Positioning System (GPS) receiver, or a portable storage device (for example, a universal serial bus (USB) flash drive), to name just a few. Devices suitable for storing computer program instructions and data include all forms of nonvolatile memory, media and memory devices, including by way of example semiconductor memory devices, for example, EPROM, EEPROM, and flash memory devices; magnetic disks, for example, internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this specification can be implemented on a display device (e.g., the display device of the dialysis machine 12), for example, a CRT (cathode ray tube) or LCD (liquid crystal display) monitor, for displaying information to the user and a keyboard or keypad and/or a pointing device, for example, a mouse or a trackball, by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input.

While this specification contains many specific implementation details, these should not be construed as limitations on the scope of any disclosures or of what may be claimed, but rather as descriptions of features specific to particular implementations of particular disclosures. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A method performed by data processing apparatus of a dialysis machine, the method comprising:
   receiving a first signal from a conductivity detector connected to a line through which a solution of bicarbonate and fluid flows to a dialyzer of the dialysis machine, wherein the fluid flows from a fluid source, through a fluid line segment connected to the fluid source and the line, to the line;
   determining a first conductivity of the solution based on the first signal;
   receiving a second signal from the conductivity detector at a time after receiving the first signal;
   determining a second conductivity of the solution based on the second signal; and
   determining that solid bicarbonate in a container through which the solution flows is approaching a level insufficient to maintain the solution at a conductivity suitable for flowing though the dialyzer, based on a determination that the second conductivity is less than the first conductivity by at least a threshold amount.

2. The method of claim 1 further comprising:
   based on a determination that the second conductivity is less than the first conductivity by at least the threshold amount, providing an alert to a user.

3. The method of claim 2, wherein the alert is provided to the user at a period of time before the container containing the solid bicarbonate is empty.

4. The method of claim 3, wherein the alert prompts the user to replace the container.

5. The method of claim 1, further comprising:
   based on a determination that the second conductivity is less than the first conductivity by at least the threshold amount, receiving a third signal from the conductivity detector at a time after receiving the second signal;
   determining a third conductivity of the solution based on the third signal;
   determining whether the third conductivity is less than the second conductivity by at least a threshold amount; and
   based on a determination that the third conductivity is less than the second conductivity by at least the threshold amount, providing an alert to a user.

6. The method of claim 1, wherein determining each conductivity of the solution based on each respective signal comprises:
   adjusting a conductivity measurement of the solution based on the signal from the conductivity detector and a temperature of the solution.

7. The method of claim 6, further comprising:
   receiving a signal from a temperature detector connected to the line; and
   determining the temperature of the solution based on the signal received from the temperature detector.

8. The method of claim 1, further comprising storing the first conductivity for comparison to the second conductivity.

9. The method of claim 8, wherein storing the first conductivity comprises:
   receiving a preceding signal from the conductivity detector at a time prior to receiving the first signal;
   determining a preceding conductivity of the solution based on the signal;
   determining that a difference between the first conductivity and the preceding conductivity is within a threshold amount;

based on a determination that the difference between the first conductivity and the preceding conductivity is within the threshold amount, storing the first conductivity for comparing to the second conductivity.

10. The method of claim 8, wherein storing the first conductivity further comprises:
comparing the first conductivity to a threshold conductivity; and
based on a determination that the first conductivity meets the threshold conductivity, storing the first conductivity.

11. A dialysis system comprising:
a fluid source;
a fluid line segment connected to the fluid source;
a container containing solid bicarbonate, the container connected to the fluid line segment, wherein the fluid flows from the fluid source, through the fluid line segment, to the container;
a line connected to the container;
a conductivity detector connected to the line; and
a data processing apparatus connected to the conductivity detector and configured for:
receiving a first signal from a conductivity detector connected to the line through which a solution of bicarbonate and fluid flows to a dialyzer of the dialysis machine;
determining a first conductivity of the solution based on the first signal;
receiving a second signal from the conductivity detector at a time after receiving the first signal;
determining a second conductivity of the solution based on the second signal;
determining that the solid bicarbonate in the container through which the solutions flows is approaching a level insufficient to maintain the solution at a conductivity suitable for flowing through the dialyzer, based on a determination that the second conductivity is less than the first conductivity by at least a threshold amount.

12. The dialysis system of claim 11, wherein the container is a collapsible bag.

13. The dialysis system of claim 11, wherein the data processing apparatus is further configured for:
based on a determination that the second conductivity is less than the first conductivity by at least the threshold amount, providing an alert to a user.

14. The dialysis system of claim 13, wherein the alert is provided to the user at a period of time before the container containing the solid bicarbonate is empty.

15. The dialysis system of claim 11, wherein the data processing apparatus is further configured for:
based on a determination that the second conductivity is less than the first conductivity by at least the threshold amount, receiving a third signal from the conductivity detector at a time after receiving the second signal;
determining a third conductivity of the solution based on the third signal;
determining whether the third conductivity is less than the second conductivity by at least a threshold amount; and
based on a determination that the third conductivity is less than the second conductivity by at least the threshold amount, providing an alert to a user.

16. The dialysis system of claim 11, wherein determining each conductivity of the solution based on each respective signal comprises:
adjusting a conductivity measurement of the solution based on the signal from the conductivity detector and a temperature of the solution.

17. The dialysis system of claim 16, further comprising:
receiving a signal from a temperature detector connected to the line; and
determining the temperature of the solution based on the signal received from the temperature detector.

18. The dialysis system of claim 11, wherein the data processing apparatus is further configured for storing the first conductivity for comparison to the second conductivity.

19. The dialysis system of claim 18, wherein storing the first conductivity comprises:
receiving a preceding signal from the conductivity detector at a time prior to receiving the first signal;
determining a preceding conductivity of the solution based on the signal;
determining that a difference between the first conductivity and the preceding conductivity is within a threshold amount; and
based on a determination that the difference between the first conductivity and the preceding conductivity is within the threshold amount, storing the first conductivity for comparing to the second conductivity.

20. The dialysis system of claim 18, wherein storing the first conductivity further comprises:
comparing the first conductivity to a threshold conductivity; and
based on a determination that the first conductivity meets the threshold conductivity, storing the first conductivity.

21. The method of claim 1, wherein a fluid enters the container containing the solid bicarbonate and mixes with a portion of the solid bicarbonate to produce the solution of bicarbonate and fluid.

22. The method of claim 1, wherein values of the first and second conductivities of the solution indicate that the solution has a physiological pH.

23. The method of claim 1, wherein the fluid flows through the container and mixes with the solid bicarbonate in the container to produce the solution.

24. The method of claim 1, wherein a volume of the solution that flows to the dialyzer is approximately equal to a volume of spent solution that flows from the dialyzer.

25. The method of claim 24, wherein the solution is dialysate and the spent solution is spent dialysate.

26. The dialysis system of claim 11, wherein values of the first and second conductivities of the solution indicate that the solution has a physiological pH.

27. The dialysis system of claim 11, wherein the fluid flows through the container and mixes with the solid bicarbonate in the container to produce the solution.

28. The dialysis system of claim 11, wherein a volume of the solution that flows to the dialyzer is approximately equal to a volume of spent solution that flows from the dialyzer.

29. The dialysis system of claim 28, wherein the solution is dialysate and the spent solution is spent dialysate.

* * * * *

UNITED STATES PATENT AND TRADEMARK OFFICE
CERTIFICATE OF CORRECTION

PATENT NO.         : 8,906,240 B2
APPLICATION NO.    : 13/220293
DATED              : December 9, 2014
INVENTOR(S)        : Martin Joseph Crnkovich et al.

It is certified that error appears in the above-identified patent and that said Letters Patent is hereby corrected as shown below:

On the Title Page,
On page 2, column 2, item (56), under "Other Publication", delete "Pimer" and insert --Primer--.

In the Claims,
Column 12, line 22, Claim 1, delete "though" and insert --through--.

Signed and Sealed this
Twenty-first Day of July, 2015

Michelle K. Lee
*Director of the United States Patent and Trademark Office*